United States Patent [19]
Ward

[11] Patent Number: 5,196,612
[45] Date of Patent: Mar. 23, 1993

[54] ETHERIFICATION OF ISOAMYLENES BY CATALYTIC DISTILLATION

[75] Inventor: Dennis J. Ward, St. James City, Fla.

[73] Assignee: UOP, Des Plaines, Ill.

[21] Appl. No.: 829,812

[22] Filed: Feb. 3, 1992

[51] Int. Cl.$^5$ .............................................. C07C 41/06
[52] U.S. Cl. .............................. 568/697; 203/DIG. 6; 585/301
[58] Field of Search ................. 568/697; 203/DIG. 6; 585/301

[56] References Cited

U.S. PATENT DOCUMENTS

| | | | |
|---|---|---|---|
| 3,506,408 | 4/1970 | Kageyama et al. | 23/288 |
| 3,634,535 | 1/1972 | Haunschild | 260/677 A |
| 3,821,123 | 6/1974 | Germanas et al. | 252/439 |
| 4,950,803 | 8/1990 | Smith, Jr. et al. | 568/697 |

Primary Examiner—Howard T. Mars
Attorney, Agent, or Firm—Thomas K. McBride; John F. Spears, Jr.

[57] ABSTRACT

Ethers suitable for use as high octane oxygenate additives for motor fuels are produced in increased yields by a catalytic distillation process wherein a mixture of $C_5$-plus isoolefin isomers and an alcohol are charged to a catalytic distillation zone containing both etherification and double bond isomerization catalysts. Otherwise unreactive isomers are isomerized to reactive species within the zone to allow them to participate in the etherification reaction, resulting in a higher ether yield.

5 Claims, 1 Drawing Sheet

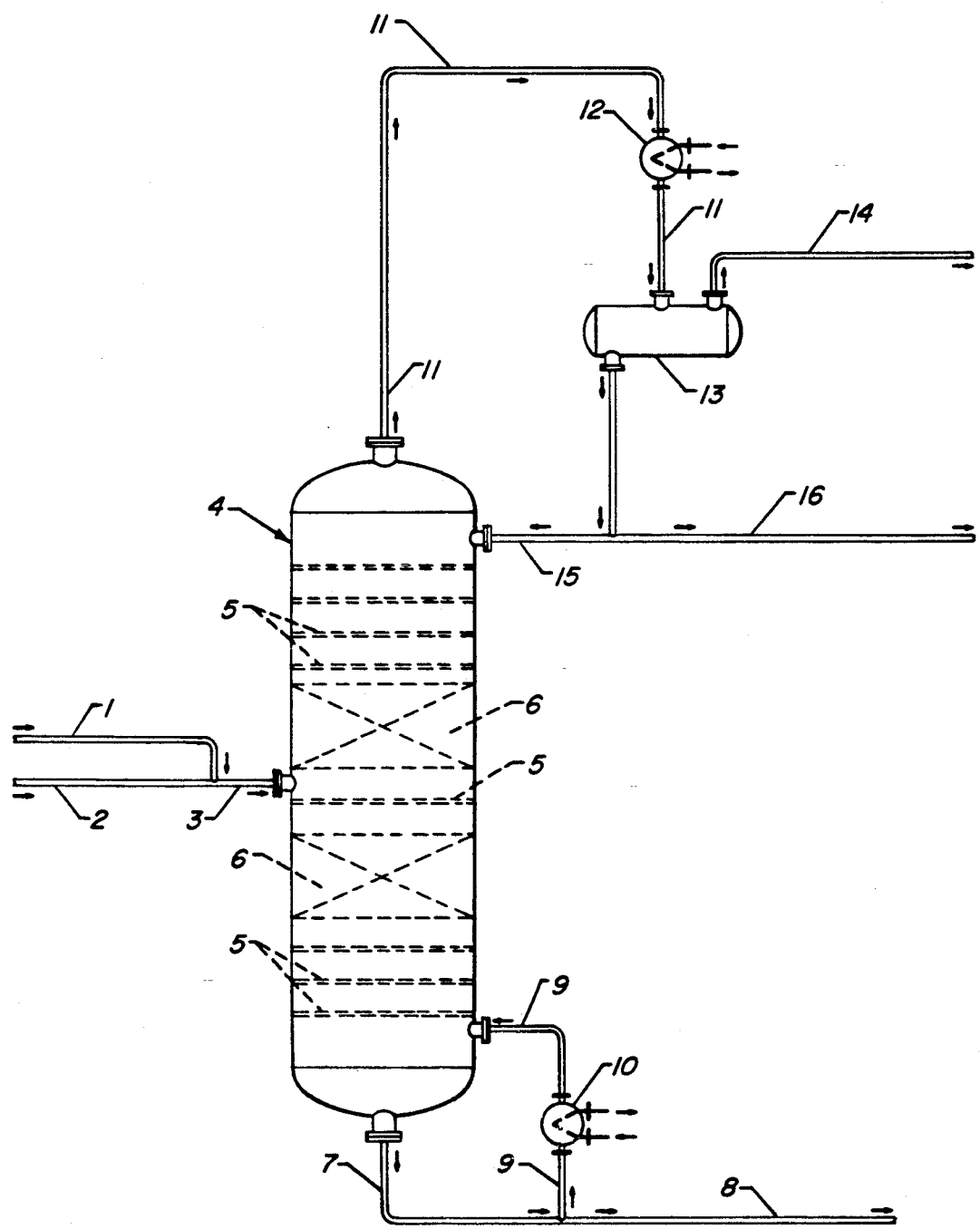

ETHERIFICATION OF ISOAMYLENES BY CATALYTIC DISTILLATION

FIELD OF THE INVENTION

The invention relates to a hydrocarbon conversion process useful in the etherification of isoamylenes or heavier C6-plus tertiary olefins. The invention also relates to the use of catalytic distillation to perform hydrocarbon conversion reactions. The invention specifically relates to a process wherein isoamylene is reacted with methanol to form a tertiary amyl ether (TAME) and isoamylene is simultaneously subjected to double bond isomerization to increase the yield of TAME.

PRIOR ART

U.S. Pat. No. 3,506,408 to O. Kageyama et al. illustrates the use of catalytic distillation for carrying out reversible liquid phase reactions such as the production of acetals and esters by the reaction of two organic feed compounds. This reference teaches the use of ion exchange resin particles located on shelves with layers of packing such as Raschig rings located above the catalyst.

U.S. Pat. No. 3,634,535 to W. Haunschild is pertinent for its showing that ethers including methyl tertiary butyl ether (MTBE) can be produced by catalytic distillation. Etherification by catalytic distillation is also described in U.S. Pat. No. 4,950,803 issued to L. A. Smith et al.

Catalysts and processes for the double bond isomerization of linear olefins are known in the art. For instance, U.S. Pat. No. 3,821,123 issued to D. Germanas et. al. teaches the use of a sulfided nickel catalyst for this purpose.

BRIEF SUMMARY OF THE INVENTION

The invention is a hydrocarbon conversion process for the production of ethers which provides a greater total yield of higher molecular weight ethers such as TAME than a conventional catalytic distillation process. One broad embodiment of the invention may be characterized as a process for the production of ethers which comprises the steps of passing a first feed stream comprising a mixture of C5-plus isoolefin isomers and a second feed stream comprising an alcohol into a catalytic distillation zone containing an etherification catalyst and also containing an olefin double bond isomerization catalyst, with the catalytic distillation zone being operated under conditions which result in the reaction of the alcohol with tertiary olefins, the isomerization of unreactive olefins to reactive tertiary olefins and the separation of compounds present in the zone into an overhead vapor stream comprising unreacted C5-plus isoolefins and a net bottoms stream which comprises a product ether.

BRIEF DESCRIPTION OF THE DRAWING

The drawing is a simplified illustration of a catalytic distillation column 4 in which the feed olefins of lines 1 are isomerized and simultaneously reacted in catalyst containing zones 6 to produce an ether removed in the product stream of line 8.

DETAILED DESCRIPTION AND PREFERRED EMBODIMENTS

The continuous quest for more economical processes for the production of petrochemicals is driving the development of etherification and alkylation processes employing "catalytic distillation". In these processes, the conversion catalyst is retained within a structure or container capable of promoting vapor-liquid contact and fractional distillation. The overall apparatus normally resembles a fractionation column. This apparatus is provided with means to effect reflux and reboiling of the apparatus. In the case of exothermic reactions such as alkylation, the heat released by the reaction is allowed to vaporize a portion of the reactants. This causes the more volatile reactants to pass upward through the overall apparatus while the less volatile product hydrocarbons flow downward in a liquid phase. This allows a facile method for separating the product from the reactants. This fractionation within the reaction zone aids in product recovery but more importantly also tends to drive the alkylation reaction to completion by removing the product and supplying fresh reactants. A very high degree of conversion can therefore be achieved by employing catalytic distillation in suitable processes including etherification. The previously cited references describe catalytic distillation in detail.

It was suggested in the past to apply catalytic distillation to a wide variety of processes such as butene isomerization (U.S. Pat. No. 2,403,672 to M. P. Matuzak) and the hydrolysis of low molecular weight olefin oxides to produce mono-alkylene glycols (U.S. Pat. No. 2,839,588 to A. S. Parker). These early disclosures did not lead to commercialization. Catalytic distillation is only now emerging as a commercially viable hydrocarbon and petrochemical processing tool.

Advantages attributed to this concept, wherein reaction products are continuously separated from the reactants and removed from the reaction zone by fractional distillation performed concurrently with the reaction, include a decrease in the capital cost of the plant needed to perform the process, the ability to achieve a higher degree of conversion, and the ability to perform processes which formerly were performed only in a batch type operation on a continuous basis. These advantages result from performing the reaction in a separation zone capable of removing the reaction products from the reactants and catalyst. Hence it is only necessary to provide one primary vessel and the reaction is not limited by chemical equilibrium.

It is an objective of the invention to provide a process for the production of ethers by catalytic distillation. It is a further objective to provide a process which increases the production of a heavy ether such as TAME from a mixture of amylene isomers such as obtained directly from a fluid catalytic cracking process. It is a specific objective of the invention to increase the yield of TAME obtained from a mixed C5 feed stream without a significant increase in capital or operation costs.

These objectives are achieved by employing both etherification and isomerization catalysts within the same catalytic distillation zone. This allows the process to replace a portion of the isoamylene consumed in the etherificaton reaction by isomerizing otherwise unreactive amylene isomers to a reactive isomer which is then consumed in the etherification reaction.

The subject process consumes two different reactants. The first is a $C_5$-$C_8$ tertiary olefin such as an amylene ($C_5H_{10}$), hexylene ($C_6H_{12}$), heptylene or Octylene ($C_8H_{16}$). It is contemplated that in the normal commercial application of the subject process these olefinic reactants, which are branched at the double bond, will be present in a mixture of other branched and straight chain olefinic hydrocarbons having the same number of carbon atoms per molecule. Therefore, the preferred feed olefin, isoamylene, will be present in the feed stream admixture with one or more other amylenes. There are five amylene isomers. I-pentene, (n-propylethylene), 2. 2-pentene, (sym-methylethylethylene), 3. 2-Me-l butene, (unsym-methylethylethylene), 4. 2-Me-2-butene, (trimethyethylene), and 5. 3-Me-l-butene (isopropylethylene). The expected feed streams to the subject process will be derived from a fluid catalytic cracking (FCC) reaction zone or a thermal cracker or similar large scale refining process and are expected to contain a mixture of all of the possible isomers in an approximate equilibrium concentration.

The second reactant is a $C_1$-$C_4$ acyclic alcohol such as methanol, ethanol, propanol or butanol. The product hydrocarbon can therefore be one of a wide variety of $C_6$-$C_{12}$ ethers including tertiary amyl methyl ether(-TAME), tertiary- amyl ethyl ether, tertiary-amyl propyl ether, tertiary-amyl n-butyl ether, methyltertiary hexyl ether and methyl tertiary heptyl ether. The preferred reactants are an amylene and methanol or ethanol.

While some of the higher boiling ethers resulting from the reaction of these reactants may not be suitable for use in gasoline, they may be useful in diesel fuel, jet fuel or other fuels or as feed stocks in petrochemical processes or as end product petrochemicals having their own utility.

The subject process can be practiced with any suitable catalysts. For both etherification and isomerization this is any heterogeneous catalyst which gives satisfactory performance in terms of conversion and selectivity for the desired reaction at the conditions required to allow fractional distillation of the reactants and products. The best catalysts to employ in the subject process will of course to a great extent depend upon the identity of the specific reactants to be converted in the process.

The preferred etherification catalyst is a macroporous acid form sulfonic ion exchange resin such as a sulfonated styrene-divinylbenzene resin as described in U.S. Pat. No. 2,922,822 having a degree of crosslinking of from about 5 to 60%. Suitable resins are available commercially. Specialized resins have been described in the art including copolymers of sulfonyl fluorovinyl ether and fluorocarbons as described in U.S. Pat. Nos. 3,784,399 and 3,849,243. Another specially prepared resin consists of the $SiO_2$-modified cation exchangers described in U.S. Pat. No. 4,751,343. The macroporous structure of a suitable resin is described in detail in U.S. Pat. No. 5,012,031 as having a surface area of at least 400 $m^2$/g, a pore volume of 0.6-2.5 ml/g and a mean pore diameter of 40-1000 angstroms. It is contemplated that the subject process could be performed using a metal-containing resin which contains one or more metals from sub-groups VI, VII or VIII of the Periodic Table such as chromium, tungsten, palladium, nickel, chromium, platinum, or iron as described in U.S. Pat. No. 4,330,679.

Various etherification process techniques, reaction conditions and product recovery methods are described in U.S. Pat. Nos. 4,219,678 to Obenous et al. and 4,282,389 to Droste et al. which are incorporated herein for this teaching.

The overall flow of the invention is illustrated in the drawing. A first feed stream comprising a mixture of amylenes carried by line and a second feed stream comprising methanol carried by line 2 are mixed together to form a combined feed stream which is passed via line 3 into the overall catalytic reaction zone 4. The incoming reaction mixture falls upon a fractionation tray 5 which also serves the dual function of a distributor for the incoming liquid reactants. The liquid-phase portion of the reactants therefore fall downward into a catalyst-containing packed bed 6 which contains both isomerization and etherification catalysts. The etherification catalyst promotes the reaction of methanol with the tertiary amylene present in the vessel at this point. This forms the desired product, TAME, and consumes isoamylene. The isomerization catalyst promotes the isomerization of unreactive amylene isomers in an attempt to reestablish an equilibrium concentration of the isomers being consumed in the etherification reaction. Liquid comprising the product TAME and some liquid phase reactants will fall onto the fractionation trays 5 located in a lower portion of the overall catalytic distillation zone 4. The conditions maintained in this section of the vessel and the rising vapors tend to concentrate the reactants into the vapor phase resulting in a purification of the TAME and the return of the reactants to the catalytic material 6.

A highly concentrated stream of TAME is withdrawn from the bottom of the zone 4 via line 7. A first portion of this bottoms stream is diverted through line 9 and a reboiler 10 to reboil zone 4 and provide the vapor necessary within the zone. A second portion of the TAME-rich bottoms liquid of line 7 is withdrawn from the process as a product stream carried by line 8.

The vapors rising upward through the inlet tray will carry reactants into a second, upper, catalyst-containing bed 6. The same etherification and isomerization reactions will occur in this catalyst containing volume as in that located below the inlet tray. The ethers produced in this zone will descend as liquid while vapor containing unreacted feed compounds and relatively inert compounds will ascend through the column 4. The fractionation trays 5 located in the upper portion of the tray will promote the separation of TAME from the ascending vapor. This will effect the production of an overhead vapor stream carried by line 11 which is rich in unreacted feed compounds of line 3. This vapor stream is passed through an overhead condenser 12 in which at least a majority of this material is condensed. The effluent of the condenser is collected in the receiver 13. Any uncondensed vapor, such as from gases dissolved in the feed stream or light contaminants, is removed from the process as an off gas stream of line 14. The liquid phase collected in receiver 13 is withdrawn and divided into the net overhead product of line 16 and the reflux liquid of line 15. The overhead liquid will contain relatively unreactive compounds such as pentane and any unreactive olefins which are not isomerized which were present in the feed stream of line 1.

There are many possible variations to the process embodiment shown in the Drawing. For instance the feed streams of line and 2 may be charged to the catalytic reaction zone separately and at other points than shown in the drawing. An internal overhead condenser can be employed instead of an external condenser.

Other possible variations relate to the construction of the vapor-liquid contacting and catalyst retention devices employed in the process. The Drawing illustrates the use of fractionation trays. These may be any suitable type of tray with a sieve tray having a conventional downcomer arrangement being suitable. Another suitable type of fractionation tray is referred to in the art as a multiple downcomer tray. This type of tray is described in U.S. Pat. No. 3,410,540. Those portions of the overall vessel devoted to fractionation can alternatively contain structured or dumped packing material and suitable liquid distributors. The preferred method of retaining the catalyst is through the use of the corrugated structural devices described in U.S. Pat. No. 5,073,236, which is incorporated herein by reference for its teaching in regard to the structure and utilization of this catalyst packing system. These devices provide a means to evenly distribute the catalyst within the desired locations in the vessel and also are effective in promoting vapor-liquid contacting.

While a structured catalyst retention device resembling structure column packing is preferred, there are other methods of retaining catalyst within the column which should also prove effective. For instance it is known that the catalyst may be retained upon the surface of perforated trays by the use of screens or bags or other particle retention means. It is also known that catalyst may be retained within downcomers used to convey liquid between fractionation trays.

The two different catalysts employed in the subject process may be physically admixed within the same retention device or they may be present in separated devices located next to one another, in layers or in separate zones at different levels or locations in the overall catalytic distillation zone. It is also contemplated that future catalyst developments may yield a single catalyst which will accelerate both the etherification and isomerization reactions.

Olefin double bond isomerization of olefinic hydrocarbons may be performed using the sulfided nickel on alumina catalyst of U.S. Pat. No. 3,821,123 which is incorporated herein for its teaching on this process. The process is operated at a temperature of 25 to 200° C., a pressure of atmospheric to 30 atmospheres, a liquid hourly space velocity of about 1 to 10 and a hydrogen concentration above 0.1 mole per mole of feed olefin. The subject invention can also be performed using other isomerization catalysts. For instance U.S. Pat. No. 4,499,326 teaches the isomerization of butenes over a catalyst comprising a crystalline borosilicate molecular sieve.

One embodiment of the subject invention can accordingly be characterized as an apparatus for the production of ethers by catalytic distillation which comprises an enclosed vertical vessel containing fractional distillation equipment located in at least its upper and lower portions, and also containing at least one bed of catalyst, with the vessel containing at least one olefin double bond isomerization catalyst and at least one etherification catalyst, with the catalysts being held in active communication with the fluids within the vessel, means to feed and distribute feed streams and to remove at least one net bottoms stream and the equipment needed to reboil and reflux the vessel.

Temperatures which are suitable for use in the subject process may be the same as those employed in a conventional etherification process. The combination of temperature and pressure must be selected to maintain a portion of the compounds in the reactor present as liquids since the etherification reaction is a liquid phase reaction and is needed for distillation. Vapor is desired only as necessary to effect distillation. Suitable temperatures are from about 30° to about 140° C., especially from about 50° to about 100° C. Pressures which are suitable for use herein preferably are above about 1 atmosphere but should not be in excess of about 130 atmospheres. An especially desirable pressure range is from about 10 to about 40 atmospheres. The concept of space velocity does not apply to catalytic distillation. The reactants should be fed to the vessel in the proper stoichiometric ratio at a rate equal to their rate of consumption therein, which is most easily measured by monitoring the rate of ether production.

The following is an example of the subject process: a mixture comprising isopentane, 2 methyl butene 2 methyl butene 2 and 2 methyl butene 3 is fed along with methanol and a small amount of hydrogen (less than 0.1 mol per mol of hydrocarbon charge) to reactor 5 via line 4. The reactor vessel contains a sulfonated poly divinyl benzene (such as Amberlist 300) in physical mixture with another catalyst such as nickel on alumina that has been reduced and partially sulfided as taught in U.S. Pat. No. 3,821,123 for isomerizing the double bond of the olefin. The conditions in the reactor include a pressure required to produce liquid phase materials, normally between 3 and 30 atmospheres with a preferred range of 4 to 10 atmospheres; and a temperature in the range of 30 to 140° C. with a preferred range of 60 to 80° C. The methanol to isoamylene ratio is from 1.0 to 10 with a preferred range of 1.0 to 2.0 and the hydrogen to olefin hydrocarbon ratio is from 0.001 to 0.1 with a preferred range being from 0.005 to 0.04. Under these conditions, it is surprisingly found that not only do the 2 methyl butene 1 and 2 methyl butene 2 react, but also the majority of the 2 methyl butene 3 is converted to tertiary amyl ether (TAME) via intermediate conversion of the 2 methyl butene 3 to mixtures of 2 methyl butene 1 and 2 methyl butene 2, both of which are reactive with methanol over acid type catalysts.

What is claimed:

1. A process for the production of ethers which comprises passing a first feed stream comprising a mixture of isomers of a $C_5$-plus isoolefin and a second feed stream comprising an alcohol into a catalytic distillation zone containing an etherification catalyst and also containing an olefin double bond isomerization catalyst, with the catalytic distillation zone being operated under conditions which result in the reaction of the alcohol with a tertiary olefin, the isomerization of unreactive olefins to reactive tertiary olefins and the separation of compounds present in the zone into an overhead vapor stream comprising unreacted $C_5$-plus tertiary olefins and a net bottoms stream which comprises a product ether.

2. The process of claim wherein the first feed stream comprises a mixture of isoamylene isomers and the second feed stream comprises methanol.

3. The process of claim 2 wherein the etherification and isomerization catalysts are retained within a structured packing material.

4. A process for the production of ethers which comprises passing a first feed stream comprising a mixture of amylene isomers and a second feed stream comprising methanol into a catalytic distillation zone containing an acid resin etherification catalyst and also containing an olefin double bond isomerization catalyst, with the catalytic distillation zone being operated under conditions which result in the reaction of methanol with isoamylene, the isomerization of unreactive amylenes to reactive tertiary amylenes and the separation of compounds present in the zone into an overhead vapor stream comprising unreacted amylenes and a net bottoms stream which comprises a product ether.

5. The process of claim 4 wherein the isomerization catalyst comprises sulfided nickel and alumina.

* * * * *